United States Patent [19]

Peguy

[11] Patent Number: 5,322,792
[45] Date of Patent: Jun. 21, 1994

[54] PROCESS AND MACHINES FOR TRANSFORMING HOUSEHOLD WASTE

[75] Inventor: Guy Peguy, Rabastens de Bigorre, France

[73] Assignees: Tucker Hughes, Inc., Bethel, Conn.; Seuratec, S.A.R.L., Rabastens de Bigorre, France

[21] Appl. No.: 822,443

[22] Filed: Jan. 17, 1992

Related U.S. Application Data

[63] Continuation-in-part of Ser. No. 687,295, Apr. 18, 1991, abandoned.

[51] Int. Cl.$^5$ .................. C12M 1/12; C12M 1/02; C05F 9/02
[52] U.S. Cl. .................. 435/311; 435/316; 71/9; 71/901
[58] Field of Search ............ 71/9, 10, 901; 435/287, 435/311, 316

[56] References Cited

U.S. PATENT DOCUMENTS

| | | | |
|---|---|---|---|
| 2,952,492 | 9/1960 | Finn | 406/71 |
| 3,041,157 | 6/1962 | Crane et al. | 71/901 |
| 3,451,781 | 6/1969 | Greene | 71/901 |
| 3,930,799 | 1/1976 | Eweson | 23/259.1 |
| 4,050,917 | 9/1977 | Varro | 71/901 |
| 4,846,975 | 7/1989 | Kelyman | 71/901 |
| 5,071,075 | 12/1991 | Wiens | 71/14 |

FOREIGN PATENT DOCUMENTS

1105143 3/1968 United Kingdom.

*Primary Examiner*—Ferris Lander
*Attorney, Agent, or Firm*—Ostrager, Chong & Flaherty

[57] ABSTRACT

An apparatus for transforming an input garbage mixture into separate fermented and non-fermented output products has a fermentation stage for depositing an input garbage mixture into non-compacted swathes to allow fermentation of the fermentable, organic waste materials therein, an input stage for loading the garbage mixture, and at least one grinder/separator stage having a grinder for grinding the garbage mixture into smaller particles and a separator with a screen of a selected mesh size for separating ground waste particles up to the selected mesh size as a fermented output product, and conveying the remainder of the particles to a reject output as a non-fermented output product. Fermentation of the input garbage mixture allows for organic maturation of the fermentable, organic waste materials in the mixture, as well as softening and rendering the fermented materials more susceptible to being broken up into small particles in the grinder/separator stage. The input stage is equipped with a hopper, a pulsed air dryer, and a magnetic drum for picking off ferrous materials. In a preferred configuration, the grinder has three rotating axles in triangular arrangement carrying chains mounted in rows thereon with hardened tips on their free ends. Successive grinder/separator stages are used to reduce the particles to the desired output size, with the separator of each subsequent stage having a progressively finer mesh size. A pulverizer/grinder stage pulverizes the reject output (mostly plastics) into smaller particles. The pulverized particles can be compressed and heat molded to form fence parts, paving blocks, road bedding materials, etc. A modified version of the grinder is used for shredding old tires into rubber particles that can be compression-molded into usable items. The invention includes the related processes and processed products.

10 Claims, 10 Drawing Sheets

PROCESS AND MACHINES FOR TRANSFORMING HOUSEHOLD WASTE

This application is a continuation-in-part of Ser. No. 07/687,295, filed Apr. 18, 1991 and now abandoned.

FIELD OF THE INVENTION

This invention generally relates to a process and machines for the transformation of household waste to usable output products, particularly, to an organic product for fertilizing soil derived from fermentable materials in the waste, as well as other products for industrial uses derived from non-fermentable materials in the waste.

BACKGROUND ART

In conventional processes for handling garbage, household waste that has been collected from urban areas is collected and deposited in a pit. Then, the waste material is roughly crushed and fragmented in order to facilitate incineration or stocking in landfills. Some processes seek to convert the organic waste materials in the garbage mixture to a usable fertilizer product by grinding the garbage to separate the organic materials from the remainder of waste materials. The remainder is not reused, but is then stored or buried in the ground.

Various machines are known for breaking up and grinding garbage into smaller aggregates or fragments. For example, U.S. Pat. No. 2,471,811 shows a grinder/slasher having two rotating axles arranged in the same horizontal plane carrying mechanical link chains which are driven in moving contact with each other over their whole lengths for grinding input garbage materials into smaller pellets that are recovered through a screen. In U.S. Pat. No. 2,952,492, a grinder system employs three axles turning in the same direction, two of them in the same horizontal plane, carrying mechanical chains which work over their entire lengths. Great Britain Patent 1,105,143 shows grinders equipped with blades mounted on parallel, rotating axles. French Patent 2,299,086 shows a grinder with jagged disks carried on an axle driven in rotational and axial movements for grinding large plastic materials.

The prior art systems employing mechanical chains have problems in that the chains can become snarled, and are subjected over their whole lengths to high levels of wear and deterioration. Moreover, the prior art systems do not have provision for readily separating the fermentable waste from the non-fermentable waste materials so that a fertilizer product as well as various other products for industrial uses can be obtained.

SUMMARY OF THE INVENTION

In accordance with the present invention, an apparatus for transforming an input garbage mixture of fermentable, organic waste materials and non-fermentable and/or non-organic waste materials into separate output products, comprises:

an input stage for initially grinding the input garbage and optionally mixing it with organic or chemical additives prior to fermentation;

a fermentation stage for depositing an input garbage mixture into non-compacted swathes to allow fermentation of the fermentable, organic waste materials therein;

an input stage for loading the garbage mixture from the fermentation stage and conveying it to a grinder; and a grinder/separator stage including a grinder for grinding the garbage mixture conveyed from the input stage into smaller particles, and a separator having a screen of a selected mesh size for separating ground waste particles up to the selected mesh size falling therethrough as a fermented output product, and for conveying the remainder of the ground waste particles not falling through the screen to a reject output as a non-fermented output product.

Fermentation of the input garbage mixture allows for organic maturation of the fermentable, organic waste materials in the mixture, as well as softening and rendering the fermented materials more susceptible to being broken up into small particles in the grinder/separator stage. In the preferred embodiments, the input stage is equipped with a hopper for loading the garbage mixture on a conveyor which conveys the garbage mixture to the grinder, a pulsed air dryer for at least partially drying the garbage mixture, and a magnetic drum for picking off ferrous materials.

The grinder of the grinder/separator stage has three counter-rotating axles carrying chains arranged in rows thereon and provided with hardened tips on their free ends that pass in close proximity to those of the other axles. Successive grinder/separator stages may be used, with the separator of each subsequent stage having a progressively finer mesh size so that the fermented output product from the previous stage is ground into smaller particles and separated from the larger reject materials. The separator may be in the form of an inclined, rotating trommel, and may be equipped with a rotating brush or air nozzles for cleaning the screen. Warm air pulsers may be used for drying the garbage mixture conveyed through the separator.

A separate pulverizer/grinder stage is provided for pulverizing the reject output into smaller particles for various industrial uses. This stage is formed with a rotating cylinder having a rotating axle therein carrying grinder chains with hardened tips. The axle is arranged off-center from the center axis of the cylinder, and the tips of the whirling chains pass close to the cylinder wall on one side. The cylinder walls have holes perforated in them to pass particles of a selected size. The pulverized particles can be compressed and heat molded to form fence parts, paving blocks, road bedding materials, etc. A modified version of the grinder is used for shredding discarded tires into rubber particles.

The invention includes the associated processes for transformation of household garbage into separate output products, and also encompasses products produced by such equipment and processes, including organic fertilizer for enriching soil, pulverized plastic particles, and rubber particles for various industrial uses.

Other objects, features and advantages of the present invention will be apparent from the following detailed description of the preferred embodiments with reference to the drawings, of which:

DETAILED DESCRIPTION OF THE INVENTION

Household waste is typically a mixture of fermentable, organic waste materials, such as food wastes, paper, and cellulose packaging materials, and non-fermentable and/or non-organic waste materials, such as plastic packaging materials, fabrics, ferrous and non-ferrous objects, batteries, synthetic materials, etc. As is typical in garbage recycling processes, the household waste is collected in garbage bags and deposited in a pit. The garbage is transferred with a grapnel to a hopper that has a mobile bottom or into a paddle feeder for initial sorting. The hopper or paddle feeder is equipped with a shaker or agitator that breaks the bags and regulates the flow of material. The matter that comes out of the hopper or feeder falls on a transporter conveyor where it becomes spread out. On each side of the conveyor, employees or automated apparatus can manually pick through and remove certain large, dangerous, or undesirable objects, such as combustible cans, containers of toxic materials, batteries, tires, fabrics, ferrous and non-ferrous objects, non-fermentable items, etc., without slowing down the flow. Removal of the undesirable objects avoids the risk of bursting containers or dispersion of toxic materials or other dangerous items. Ferrous objects can be removed with an electromagnetic drum over the conveyor.

For the practice of the present invention, the conventional breaking up of the garbage and removal of undesirable elements are used to provide a rough, input garbage mixture. It is not necessary to remove the plastic matter at this stage, since the invention provides for its separation and removal as a usable output product.

Figure 1:
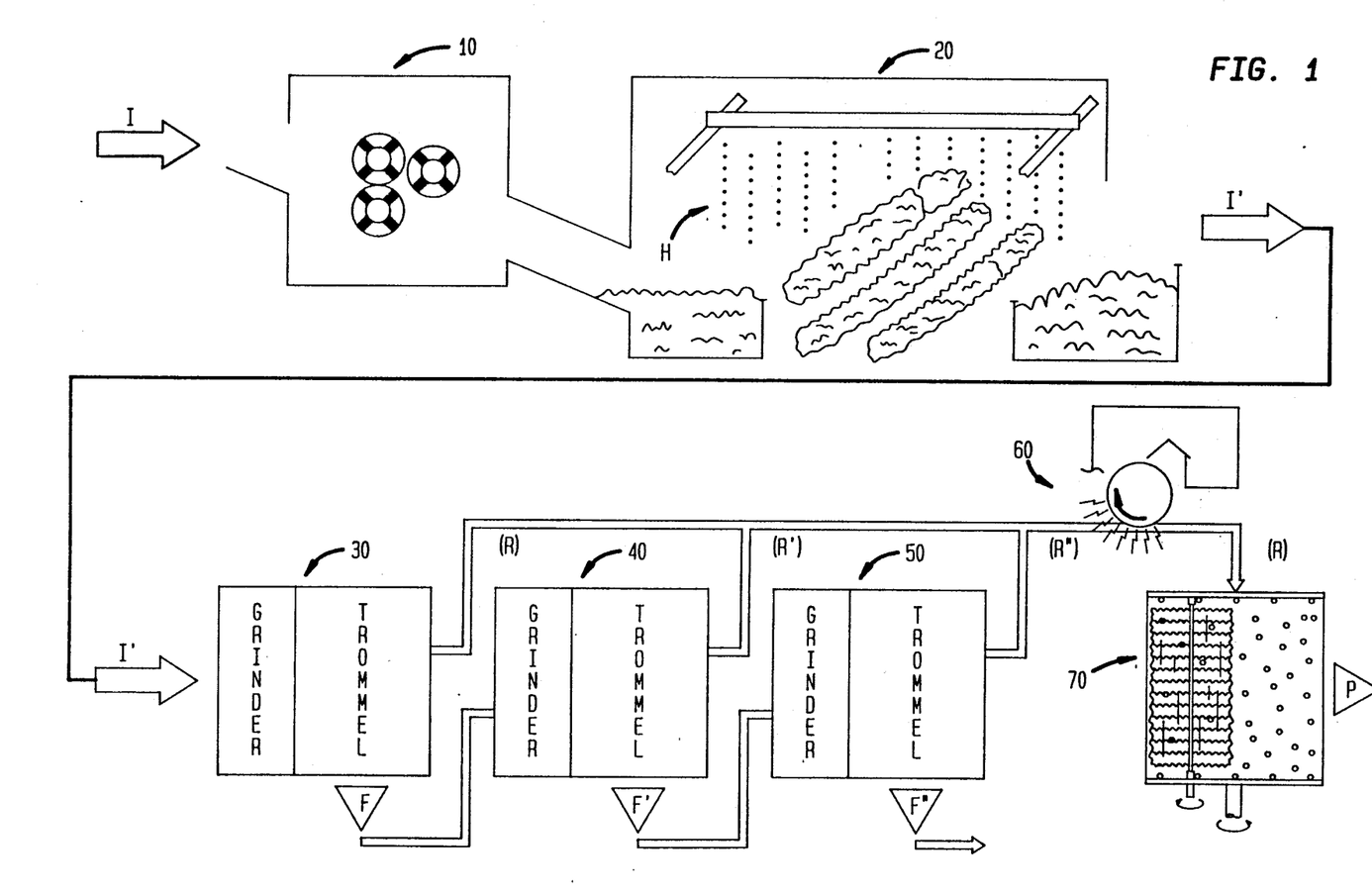
FIG. 1 is a schematic drawing of an overall process and machines for transformation of household waste to usable output products, in accordance with the present invention.

Referring to FIG. 1, the overall process and machines for transformation of household waste to usable output products are shown schematically. The input garbage mixture I obtained from household waste may be ground into smaller, more tractable fragments using an initial fragmenter/grinder unit 10. The grinder unit 10 is preferably of the multi-axle type which is a particular feature of the present invention. As shown in more detail in FIG. 4, the grinder unit is preferably equipped with three rotating axles 11a, 11b, 11c carrying chains C distributed along their lengths. The three axles are arranged in an equilateral or isosceles triangle configuration. The axles 11a and 11c are arranged above and below each other at an upstream position receiving the input garbage mixture and are driven in counter directions. The third axle 11b is arranged at a downstream position equidistant from the other two axles and is rotated in the same direction as axle 11a to propel the exiting material in a downward direction.

Figure 4:
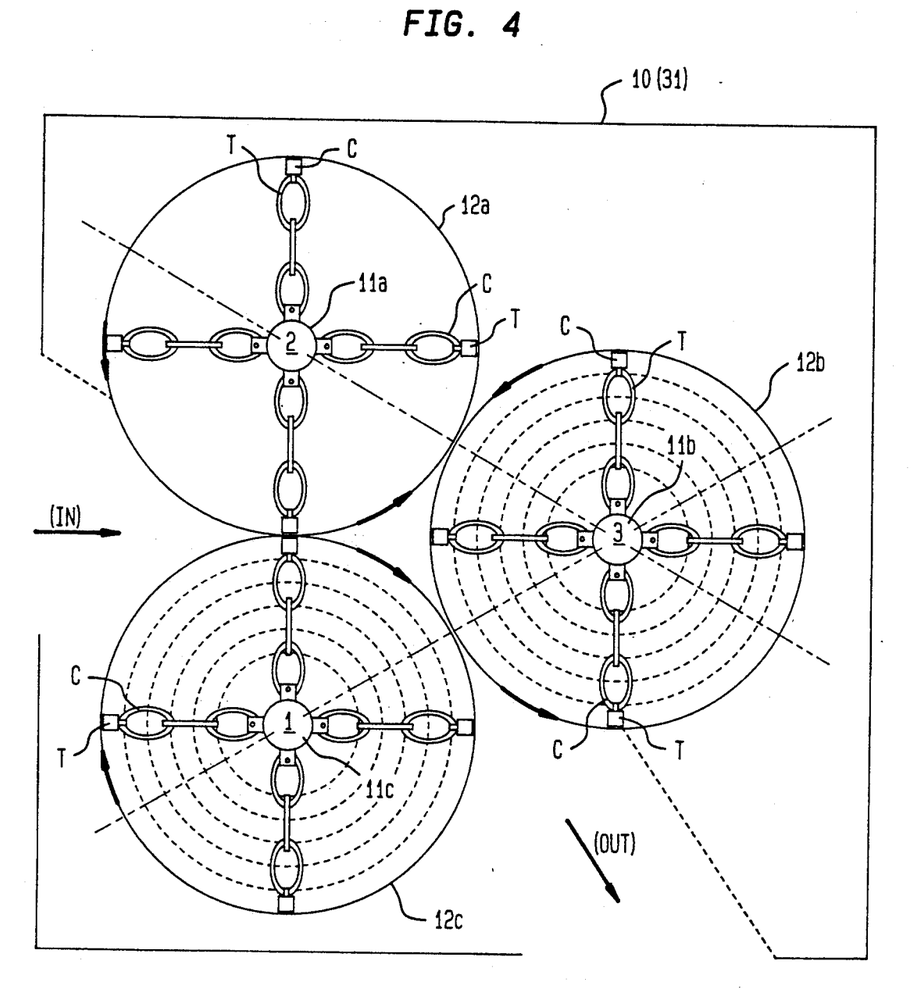
FIG. 4 is a sectional view of a preferred form of grinder unit having three axles carrying chains with hardened tips for breaking up the input garbage mixture into smaller particles.

On each axle, a plurality of chains C are arranged in longitudinal rows. In this example, four rows are spaced equidistantly around the four quadrants of the axle. One end of the chains is attached to the axle, while the opposite free end carries an interchangeable hardened tip T. Each of the axles is powered by an electric motor with a speed that can be varied. In the preferred embodiment, the lower axle 11c in FIG. 4 is driven in counter-rotation with twice the speed of the other axles, for example, at 2000 rpm compared to 1000 rpm for the others, so that its chains impact the garbage material twice per rotation compared to once per rotation for the others. The speeds of the axles and the length, number, and thickness of the chains may be varied according to the result at each stage or the fineness of particles desired.

The centrifugal force on the chains attached to the rotating axles stretches them out, so that the hardened tips T form respective cylindrical shapes that have "variable geometry" as the tips make high-speed contact with the incoming garbage. Partial interior casings or housings 12a, 12b, 12c help confine the matter being processed in the vicinity of the chains. That is, the chains will give way around a hard object passing through that is not pulverized, and will then immediately resume their initial shape. The length of the chains and the spacings of the axles are chosen so that the tips T of each axle are separated by a small distance from those of the other axles. The preferred length of the chains, from their attachment points on the axle to the tips, is about 35 cm. The distance between the tips of the axles may be varied, e.g., between 1 mm to 50 mm, by adjusting the position of the axles on slide bars along the dashed lines indicated in the drawing. This arrangement allows the incoming garbage to be shredded or pulverized by the high kinetic energy of the whirling tips, while avoiding excessive wear and deterioration on the chains. The triangular positioning and counter double-speed action creates a vacuum that helps dry the material and passes the material through without the need for air equalization. The three-axle arrangement provides an enhanced performance and granularity over conventional grinders, and has an efficiency that makes use of a greater number of axles unnecessary.

Simultaneously with the household waste, other organic matter, such as sludge, slaughterhouse waste, sawdust, bark, all kinds of farm or agricultural debris, etc., may be introduced into the fragmenter/grinder unit 10 to increase the organic materials content of the garbage mixture. Because it could contain heavy metals, sludge should generally be limited to no more than 10% of the weight of the household waste. The added organic matter becomes thoroughly broken up and mixed with the household waste by passage through the fragmenter/grinder unit 10. The waste fragments may be passed through a second fragmenter/grinder unit if further reduction of the fragment size is desired. The input through the initial grinder unit 10 may also be humidified somewhat, e.g., with water content of about 8% of the input tonnage. This may be obtained from blood and fluids in slaughterhouse waste and/or water. The input of organic matter, along with the humidification done during fragmentation, facilitates the subsequent fermentation process.

As shown in FIG. 1, fermentation of the input garbage mixture is accomplished in the next stage, indicated by the numeral 20, of the overall transformation process. The input waste that has been fragmented by its passage through the fragmenter/grinder unit 10 is picked up, for example, by a grapnel or mover machines, and laid out in non-compacted, uncovered swathes in a sheltered structure. The waste matter is periodically humidified and turned in an elevated, ambient temperature. Humidification may be provided by sprinklered water, indicated by the letter H. It is very important that the fermentation-maturation process take place in a sheltered structure to allow absolute control of temperature, air pressure, and water content, and to control airborne debris and odors. Also, the introduction of bacterial enzymes with the sprinklered water for humidification can considerably reduce the fermentation time.

The recommended amount of water for the fermentation process is about 30 to 35% of the total weight being processed. Application of this amount of water is preferably spread out over about 60 days. A maturation period of about 20 days afterwards is recommended to obtain a stabilized product. The first turnover of matter in a swath should take place about 30 days after the waste has been laid down in swathes. The second turnover is done after about 45 days, and the third after about 60 days. The watering should be done once a week, spread out evenly over 24 hours. The dirty water passing through the swathes can be directed to a watertight pit and recovered after allowing sediment to deposit, then reused for more watering. The maturation is complete when the exothermic heat in the swathes reaches a temperature about equal to the elevated, ambient temperature in the building. The fermented and maturated waste is taken and stocked into a pit for the subsequent processing stages.

The rough, fermented material processed from typical household waste has the following composition and properties:

TABLE 1

| Material Content: | |
| --- | --- |
| Water: | 40% to 45% |
| Ferrous: | 1% |
| Non-ferrous: | 3% |
| Plastics: | 8% to 14% |
| Fermentable: | 40% to 50% |
| Chemical and Physical Analysis: | |
| Ph: | 7.4 to 7.8 |
| Resistivity: | 700 to 1000 cm |
| Dry content: | 75% to 85% |
| Fertilizer minerals: (in g/kg per dry product) | |
| Na 20 - | 0.60 to 1.30 |
| K 20 - | 1.60 to 2.30 |
| P 205 - | 0.18 to 0.25 |
| MgO - | 1.20 to 1.70 |
| CaO - | 21.0 to 23.0 |
| Organic matter: (in g/kg per dry product) | |
| 100 to 120: | N2 total 5.8 to 6.5 |
| C mini 50 to 60: | C/N mini 7.7 to 9.2 |
| C maxi 70 to 90: | C/N maxi 13.8 to 15.5 |
| Mineral composition: (in g/kg per dry product) | |
| Zn - | 1.5 to 2.5 |
| P (total) - | 23 to 25 |

TABLE 1-continued

| Mn - | 1.2 to 1.4 |
| --- | --- |
| Mg - | 3 to 4 |
| Cu - | 2.4 to 0.7 |
| Fe - | 30 to 34 |
| Ca - | 26 to 28 |

Figure 2:
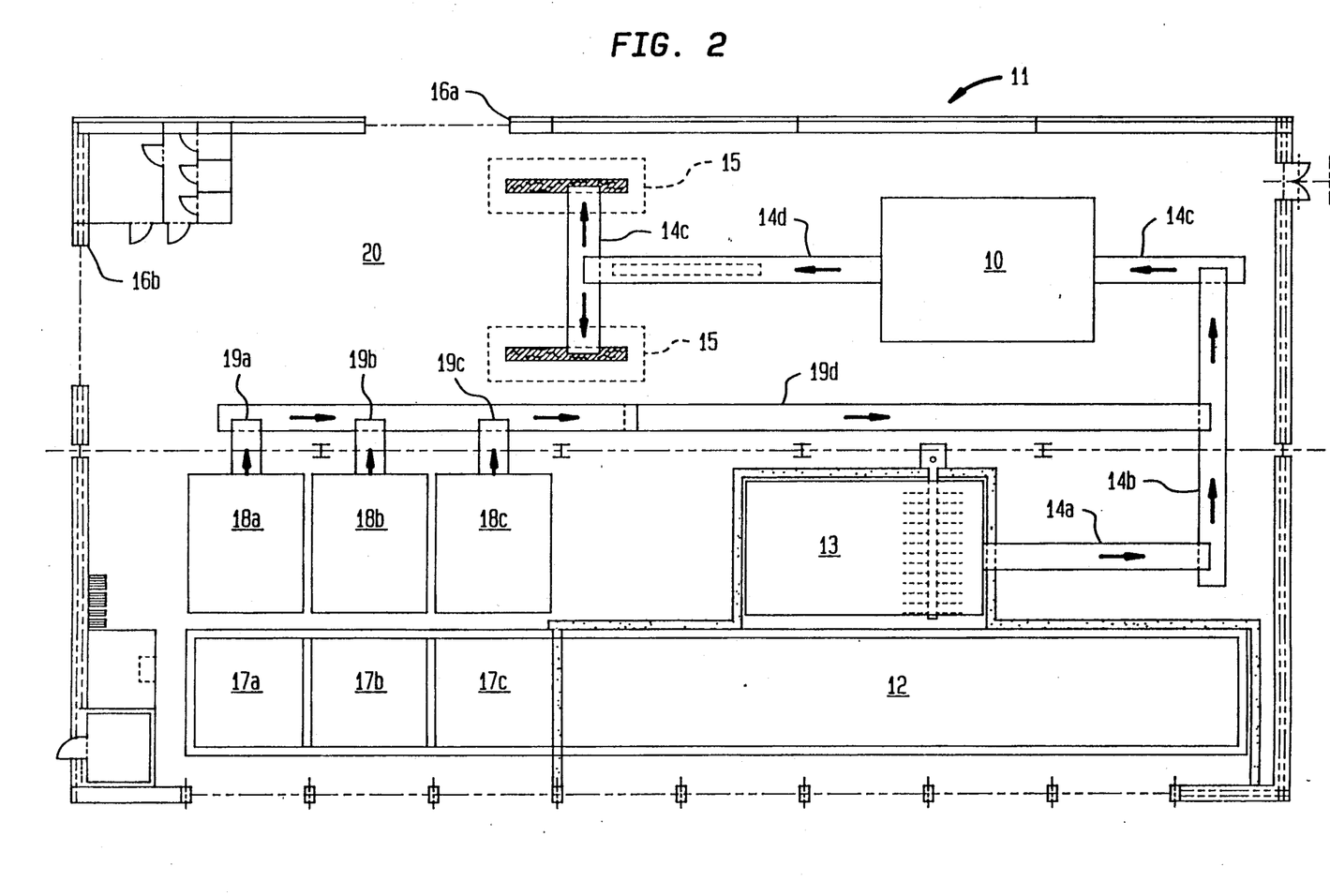
FIG. 2 is a schematic plan view of a preliminary fragmentation and mixing stage of the garbage transformation process in an enclosed structure.

In the preferred implementation of the invention, the initial fragmentation of the garbage material is accomplished in an enclosed climate-controlled structure. As illustrated in FIG. 2, the enclosed structure 11 has an input area 12 used for reception of the input garbage material through adjacent loading bays. A loader moves the garbage from the input area to a grinder 13 which breaks apart plastic bags containing the garbage and mixes the garbage. The garbage moves onto conveyors 14a where manual sorting and removal of certain items (e.g., batteries) can take place. Storage bins 17a, 17b, 17c are provided for holding desired additives, such as added organic materials (sawdust, slaughterhouse waste, etc.), added compost materials and/or fertilizer additives (nitrates, phosphoric and potassium compounds). The additives are metered through respective feeder units 18a, 18c and transported via conveyors 19a, 19b, 19c, 19d to be combined with the input garbage material. The garbage/additive mixture moves on conveyors 14b, 14c into the fragmenter/grinder 10, which grinds and mixes the garbage. The fragmented garbage is deposited via movable conveyors 14d and 14e onto flat bed trucks which drive through area 20 to exit door 16a or 16b and from there to a separate climate-controlled structure which is the fermentation area.

The fermentation area is provided with sprinklers for water and machines for turning the fermenting material. A larger fermentation area may be provided in an added or separate enclosed structure depending upon the desired volume of garbage processing. After the fermentation and maturation process is complete, the fermented garbage mixture is moved by mover machines via exit doors to the grinder/separator stages.

Referring again to FIG. 1, the fermented garbage mixture I' is passed through the subsequent processing stages, including a first grinder/separator stage 30 and successive grinder/separator stages 40 and 50, as desired, which grind and screen through the fermented, organic waste material F into successively finer particles of from 30 mm down to 1 mm size, a stage 60 for removing ferrous particles from the reject waste material R, and a pulverizer/grinder stage 70 for pulverizing plastic and other non-fermentable materials in the reject waste stream into fine particles in a range of 10 mm to 1 mm or less ("dust").

Figure 3A:
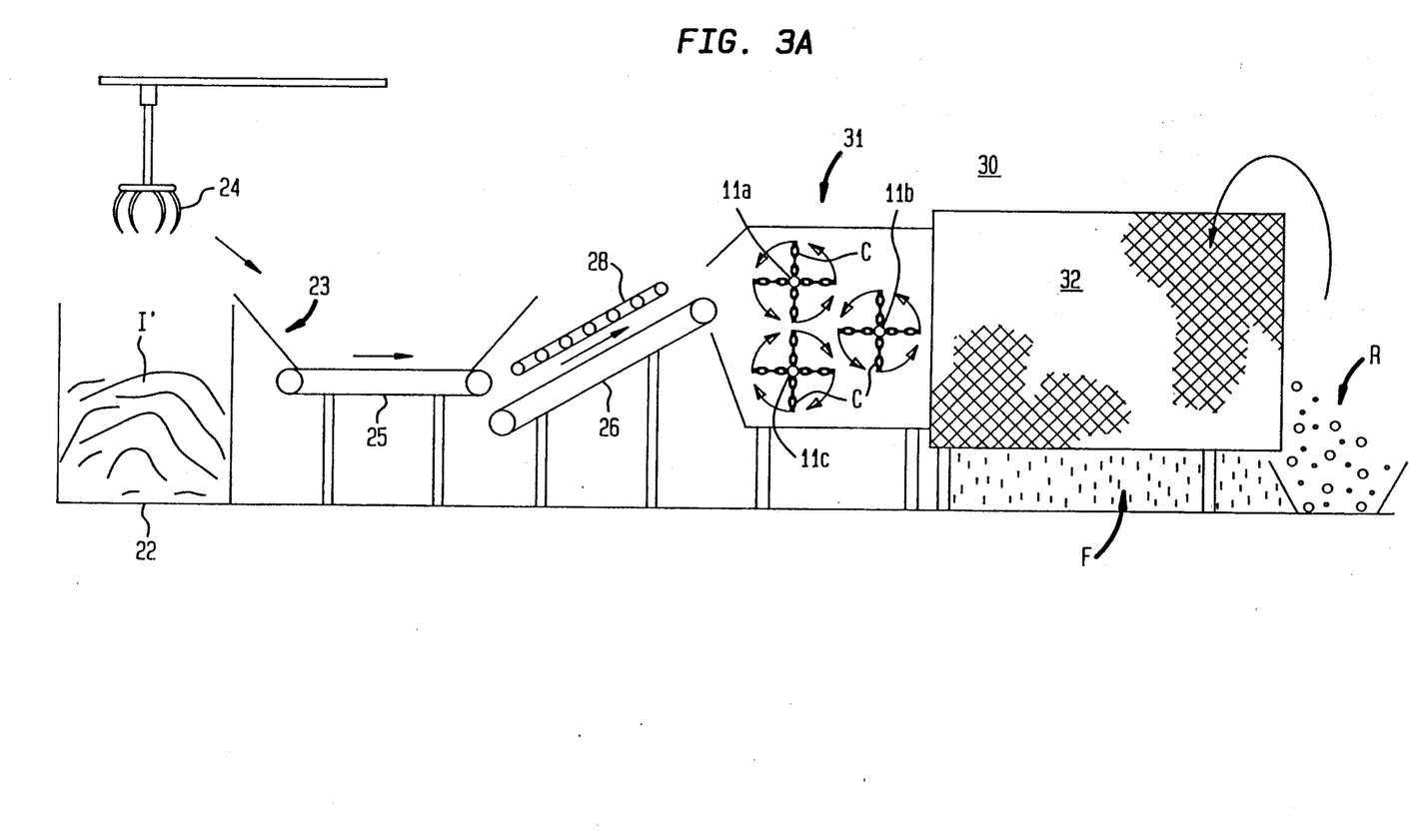
FIG. 3A is a schematic drawing of an input stage for loading and conveying the input garbage mixture to a first grinder/separator stage.

In FIG. 3A, an input stage is shown having machines for loading and conveying the fermented and maturated waste matter I' collected in a stocking pit 22 to the first grinder/separator stage 30. The matter is taken by a grapnel 24 that feeds a mobile-bottomed hopper 23 wherein a bottom conveyor 25 transports the matter to a transporter conveyor 26 which feeds the matter into the grinder unit 31 of the grinder/separator (combined) stage 30. The grinder unit 31 is of the multi-axle type, as previously described and shown in FIG. 4. As before, the grinder unit 31 has three axles 11a, 11b, 11c carrying the chains C thereon. A dryer 28, preferably a pulsed air dryer, may be positioned along the conveyor path to reduce the water content of the waste material.

The spacing between the stretched chains of the respective axles are regulated to avoid, at this particular point, excessive fragmentation. The objective here is to obtain a thorough mixing and aeration of the waste. The ability to vary the spacings between the chains that are stretched by centrifugal force assumes its full importance here. The same grinder unit can be adjusted to fragment very finely, or only lash the matter while aerating it. The aeration is important to reduce the water content from about 30 to 35% in the input matter to about 20 to 25% in the output product. The grinder unit 31 thus fragments, lashes, and aerates the waste, and feeds it into the separator unit 32 which, at this first stage, has a screen of 10 mm to 30 mm mesh. In this example, a 30 mm mesh is used.

The separator unit 32 is preferably in the form of an inclined, rotating trommel that employs a screen of the selected mesh size formed in a tunnel shape. Ground waste particles exiting from the grinder unit 31 spills down over the turning screen, and particles of the mesh size and smaller fall through the screen to provide the fermented output product F, as indicated in FIGS. 1 and 3A. The particles that are too big to fall through the screen are carried out to the end of the trommel and collected as reject waste materials R. The upper part of the trommel may be equipped with a cylindrical, rotating longitudinal brush having rigid filaments for cleaning the obstructed meshes.

In general, waste material that is organic is most likely to have been broken up and softened in the previous fragmentation and fermentation processes, and therefore will comprise most of the smaller particles that fall through the trommel screen. The larger particles that are carried through as reject waste material will be mostly inorganic and/or non-fermentable materials. The overall processing system is designed to handle a certain tonnage of waste material a day. An attempt to grind down and separate a high tonnage of waste in a single grinder/separator stage is likely to slow the throughput down to a non-viable pace. Therefore, it is desirable to have the grinding and separation process implemented with successive grinder/separator stages following the stage 30, each with a successively smaller mesh size, until the desired size of fermented output particles is obtained.

Figure 3B:
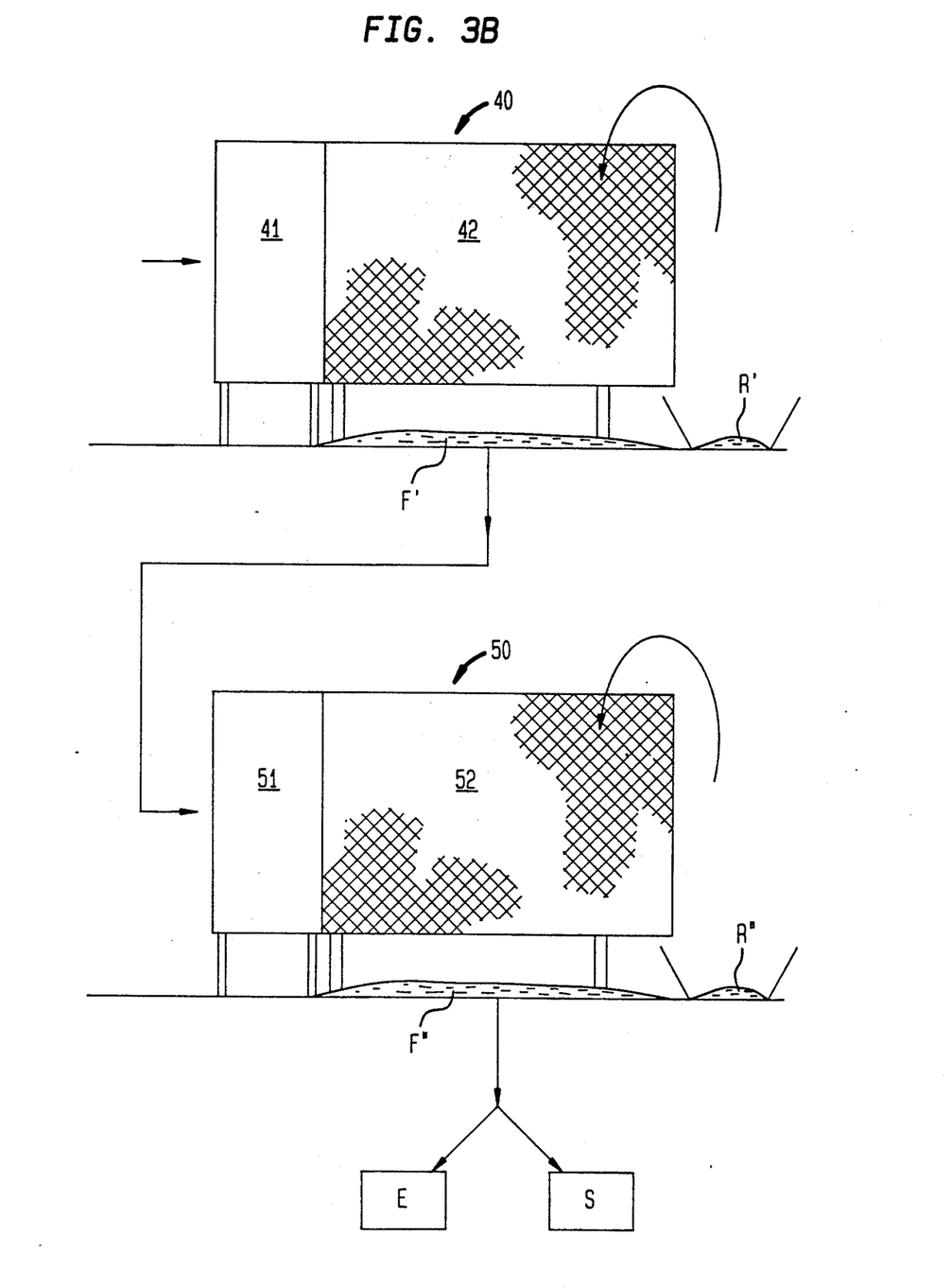
FIG. 3B is a schematic drawing of two successive grinder/separator stages for grinding the fermented output of the first grinder/separator stage to finer particle sizes.

Referring to FIG. 3B, the desired size of output particles is obtained by passing the fermented, organic output F of the first grinder/separator stage 30 (of 30 mm mesh size) to a second grinder/separator stage 40, similar in construction to stage 30, having a grinder unit 41 and a trommel 42 with a screen of 15 mm mesh size. The fermented output F' from the trommel 42 is then fed to a third grinder/separator stage 50 with a grinder unit 51 and a trommel 52 with a screen of 5 mm mesh size. A magnetic drum may be provided on the transporter path of the output F of stage 30 to the stage 40, the output F' of stage 40 to the stage 50, and/or the output F" of the stage 50, in order to remove ferrous objects that have passed through the meshes. A further grinder/separator stage (not shown) may be provided to reduce the output F" to a finer particulate size of 1.5 or 1 mm size. The number and mesh sizes of the grinder/separator stages may be varied depending upon the particular composition, output particle size, and tonnage throughput desired. The final fermented output product (here F") is then directed to a bagging station E or to a stocking place S.

The grinder units of the successive stages are similar in configuration, but the primary stage or stages are designed to be structurally stronger in order to withstand the heavier impacts and pressures of larger objects without risk of damage. The secondary stages may be structurally lighter, and have thinner chains in greater numbers rotated at higher speeds in order to grind the incoming objects finer. The grinder units produce a violent movement of air characterized by blasts and pulses as the matter impacts and is propelled by the aerotors. The fragmentation of the particles and the violent air movement transports and directs, as well as dries (reduces the water content) of the treated matter. In the event the water content is still too high, hot air (at about 50° to 60° C.) may be injected into the grinder/separator units. The trommels are covered on their sides to confine flying objects, air blasts, and reduce caloric losses.

The trommels are provided with rotating brushes with stiff bristles for keeping the metal screens from being plugged or clogged by the treated matter, which occurs particularly when the matter has a high water content. For trommels having mesh screens of finer sizes, e.g., 1.5 mm mesh, a compressed, pulsed air system may be used for cleaning in addition to the interior rotating brush. The air may be compressed to a pressure of 2 kilos/cm$^2$ and diffused with a jet ramp installed at the exterior side of the trommel. The pulsed air system may be operated continuously, intermittently, or only when the meshes become plugged.

The fermented output product is usable as an organic fertilizer for soil or compost material having a typical organic content of about 30% to 35%. A chemical and physical analysis of output product for typical processed household waste is as follows:

TABLE 2

| Chemical and Physical Analysis: | |
|---|---|
| Moisture, % of total weight: | 25.7% |
| Minerals, % of dry matter: | 69.0% |
| Organics, % of dry matter: (calcination 600° C.) | 31.0% |
| Organics, % of dry matter: (C × 1.8) | 17.8% |
| Ph: | 8.1 |
| Conductivity, dry matter/cm: | 3.1 |
| Ratio C/N: | 14.0 |
| Fertilizer minerals: (in g/kg of dry product) | |
| Nitrogen - | 7.0 |
| Carbon - | 8.5 |
| Na - | 9.6 |
| K 20 - | 5.0 |
| P 205 - | 5.4 |
| MgO - | 9.3 |
| CaO - | 123.0 |

The above typical composition conforms to the normative standard NFU 051, and can conform to the norm NFU 071 for an organic fertilizer by adding suitable amounts of nitrates (N), phosphoric compounds (P), or potassium compounds (K) by injection of organic complements either upstream in the fragmenting process, or downstream before bagging or stocking. For better soil enhancing characteristics, other additives, such as worm compost, may be added to the processed matter. A typical chemical and physical analysis of output product after injection of organic complements is as follows:

TABLE 3

| Chemical and Physical Analysis: | |
| --- | --- |
| Mineralization | 0.0% |
| Total dry matter: | 63.8% |
| Total volatile matter: | 19.5% |
| Ph: | 5.9 |
| Fertilizer minerals: (in % of dry product) | |
| Total nitrogen, Kjeldahl - | 4.0% |
| Phosphorus, in P 205 - | 5.6% |
| Potassium - | 0.5% |
| Sodium - | 0.8% |
| Calcium - | 6.9% |
| Organic carbon (m. Anne) - | 12.6% |

At the present time, large volume users of chemical fertilizers do not use organic material or organic based fertilizers because the cost is prohibitive. The mixing of chemical fertilizers with organic matter permits one to diminish the amount of N-P-K required to create a less expensive, organic based chemical fertilizer, while also including indispensable humus to the product and thereby bringing it to the soil. The fertilizer product that results from the above-described processing can have a fine granularity of 1.5 mm that bears no resemblance to the usual urban compost material. Instead, it looks like top soil, is without odor, and has a water content of 20% to 25%. Such organic fertilizer can be used with other elements in different fertilization uses in order to obtain a bio-dietetic action that will correctly satisfy the needs of plant growth. The organic fertilizer product of the present invention can revolutionize the usage of such fertilizers in agriculture, since it allows one to combine humic restitution with the input of chemical elements of N-P-K.

Referring again to FIG. 1, the reject waste materials R, R', R" are transported from the grinder/trommel stages 30, 40, 50 for further sorting, separation, and/or reduction. The reject materials represent about 10% of the input household waste. Ferrous objects that may have passed through the preliminary manual sorting or been fragmented by the grinder units are removed from the reject stream by an electromagnetic pickoff unit 60, and are stocked, baled, or sold in bulk. Hard, heavy objects may be removed by ballistic sorting in the known manner (differentiation by imparted momentum) and then deposited in a landfill or sent to special facilities for recovery, as in the case of materials such as glass, ceramic, metal objects, stones, inert objects, etc. Lighter materials remaining in the reject stream, principally plastics, fragmented glass and fabrics, may be stocked or baled for further treatment and recycling, or directed to the pulverizer/grinder stage 70 for further processing.

Figure 5:
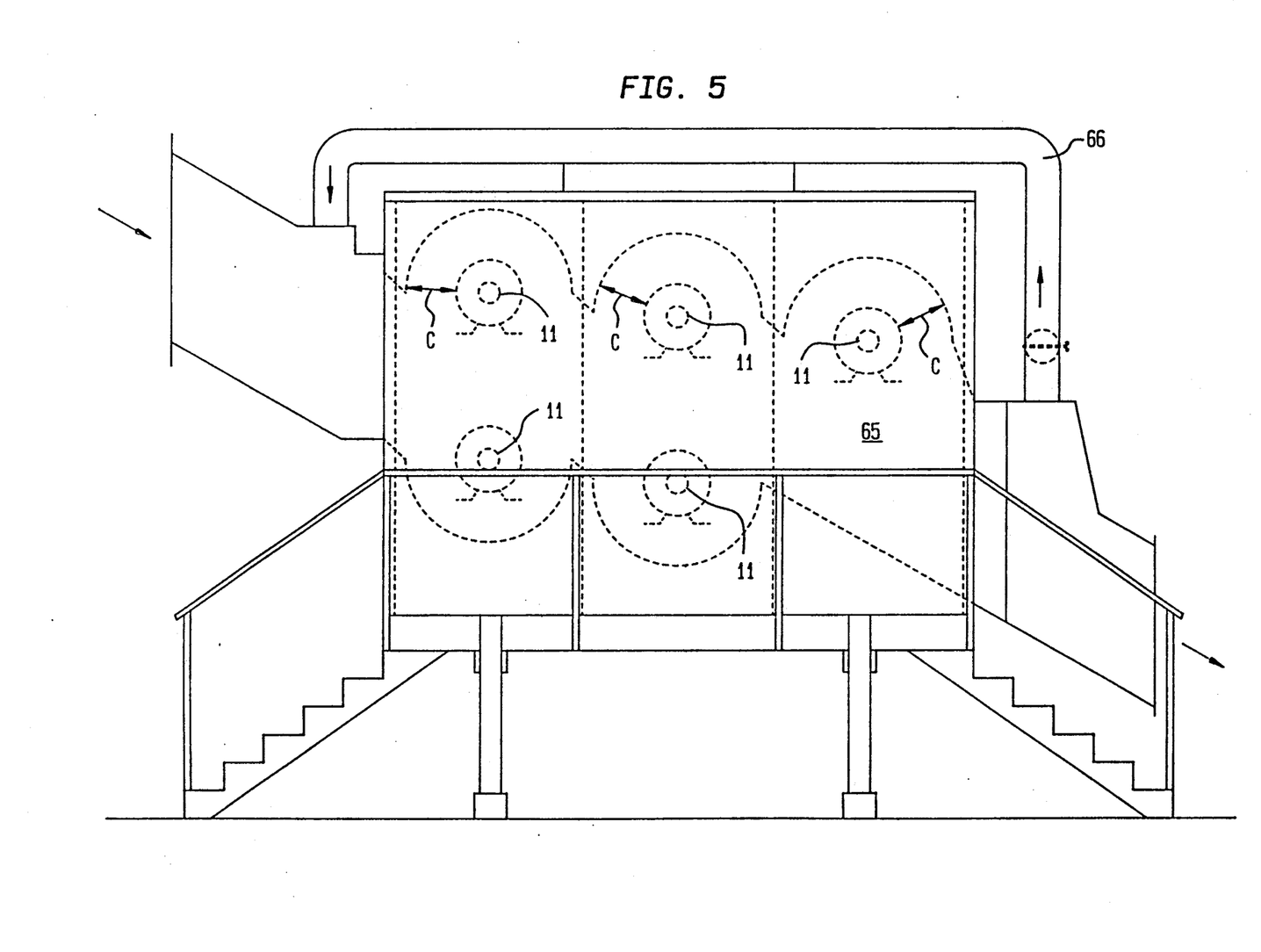
FIG. 5 is a side view of a five-axle grinder unit.

Further processing of the lighter reject waste materials may include: preliminary passage through a fragmenter/grinder unit, similar to the one described with respect to FIG. 4, to reduce and ventilate the matter; further manual sorting to remove undesirable elements not eliminated by ballistic sorting; drying in a drying drum, e.g., using circulated hot air at 50° to 60° C.; and/or passage through a secondary fragmenter/grinder unit to further break up and shake any organic matter sticking to the material. The fragmenter/grinder unit or units may be similar to that shown in FIG. 4. For greater fragmentation or grinding, a grinder unit with five rotors may be used, for example, the unit 65 shown in FIG. 5 having a return air duct 66 for equalization of air pulsations through the unit. The organic matter shaken from the fragmented material is removed by pouring the output onto a vibrating sieve having a mesh, for example, of about 1.5 mm size. A cyclonic system at the end of the vibrating sieve sucks all the remaining light elements (which are about 98% plastics at this point) to the final pulverizer/grinder stage 70 which pulverizes the material to a desired granularity. The heavier rejects not passing to this stage are stocked for disposal. They are composed mainly of insert materials representing typically about 3% of the total matter.

Figure 6:
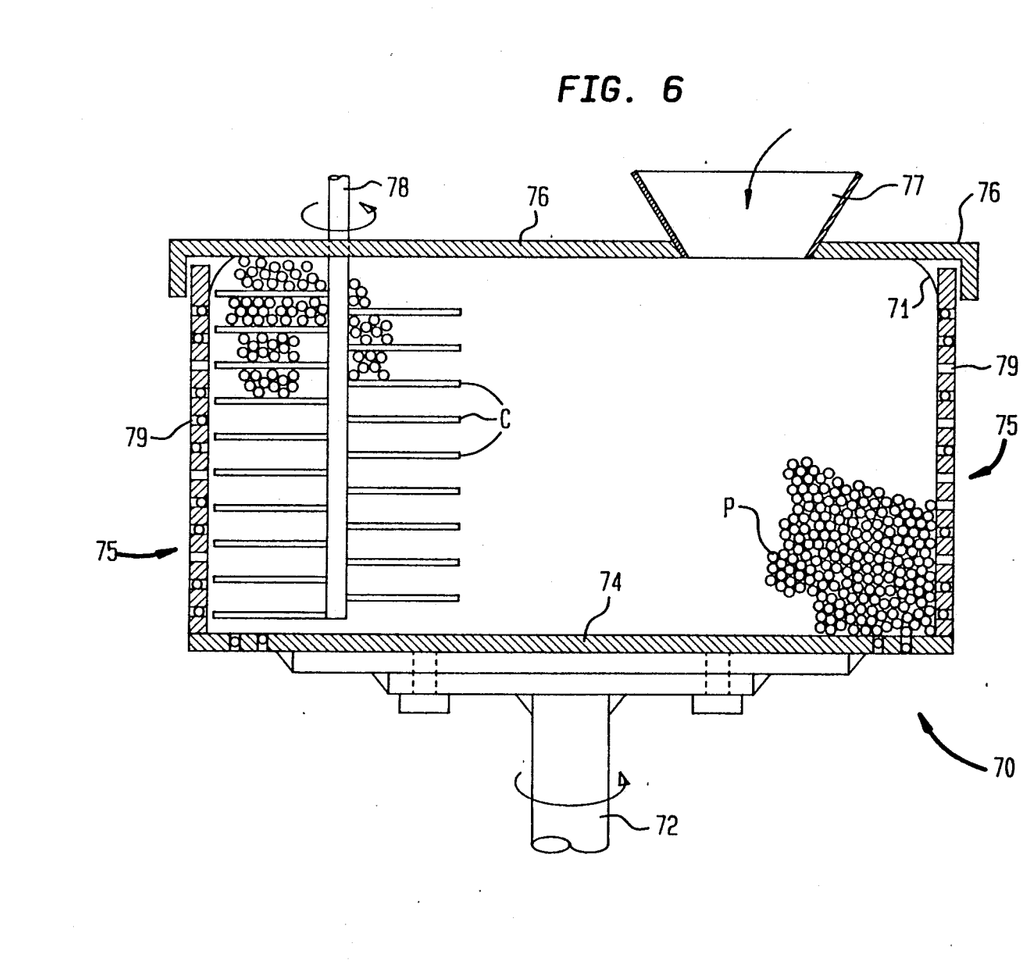
FIG. 6 is a sectional view of a pulverizer/grinder stage having a vertical container cylinder and axle with grinder chains for pulverizing non-fermented reject output into finer particles.

An illustration of a pulverizer/grinder stage 70 specially constructed for this purpose is shown in FIG. 6. The grinder unit has a bottom plate 74 affixed to vertically-oriented cylindrical walls 75, a top cover 76, and an inlet 77 for the incoming plastics material. The bottom plate and cylindrical walls is a rotating body driven by the drive axle 72. The top cover 76 is set so that it nearly touches the rotating cylinder walls. An 0-ring joint/gasket 71 prevents leaks between the rotating cylinder and the cover. At an off-center position from the body axis, a rotating arbor with chains is provided in the form as previously described having chains C driven at a high speed by the driving arbor 78. The chains are stretched out in a cylindrical shape by the centrifugal force of rotation. The arbor 78 with chains C and the cylindrical container 75 are driven in counter-rotating directions, or may be driven in the same direction but at differing speeds. The length of the chains C and rotor position are selected so that the tips are spaced by a slight gap from the nearest side of the cylindrical walls 75. The cylindrical walls 75 have perforated holes 79 of a selected size, e.g., between 1 mm and 10 mm, for passing the pulverized particles therethrough. The assembly is mounted on slide bars to permit changing of the worn tips of the chains or parts of the cylindrical container.

Figure 7A:
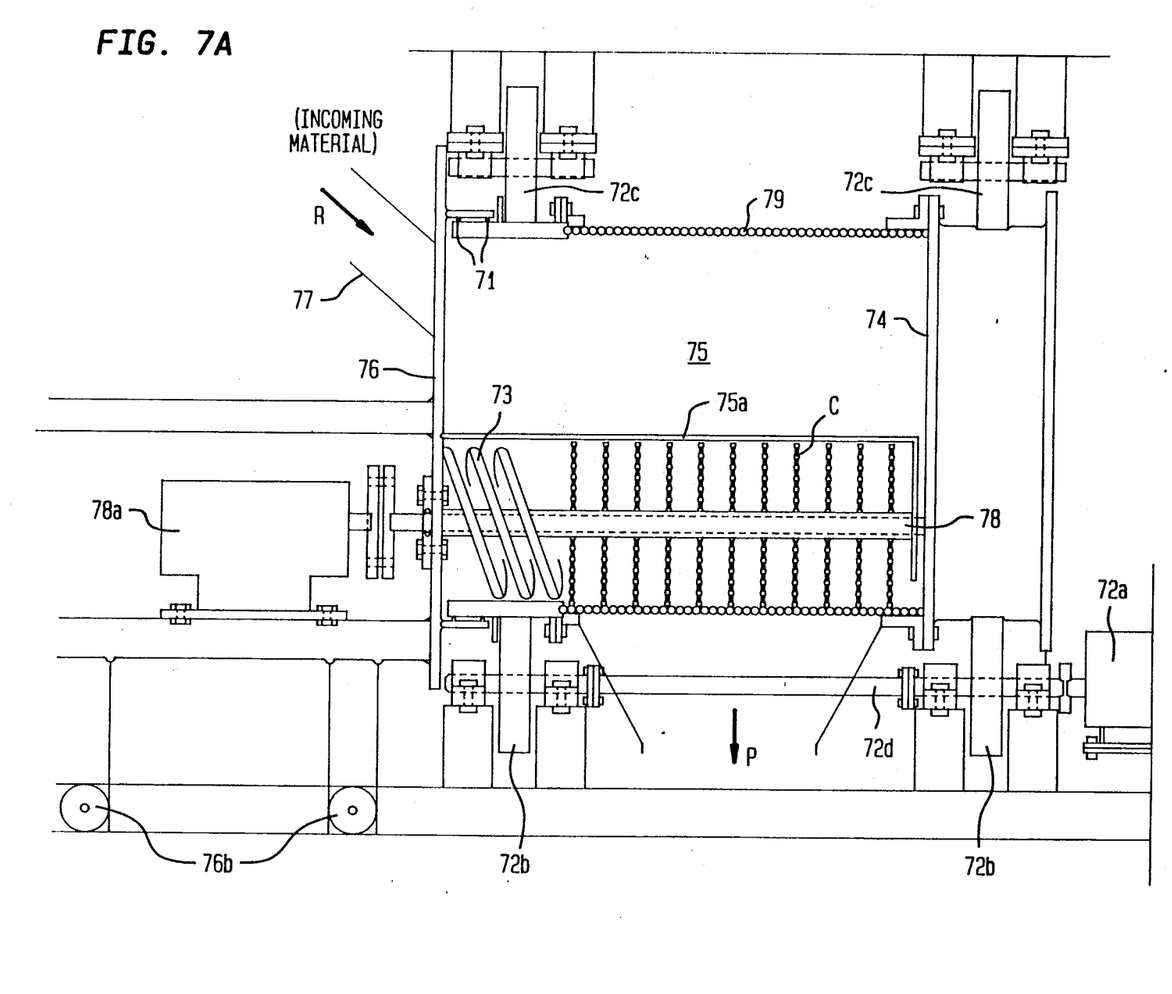
FIG. 7A is a sectional view of another version of the pulverizer/grinder stage having a horizontal container cylinder, axle with grinder chains, and counter-rotating brush.
Figure 7B:
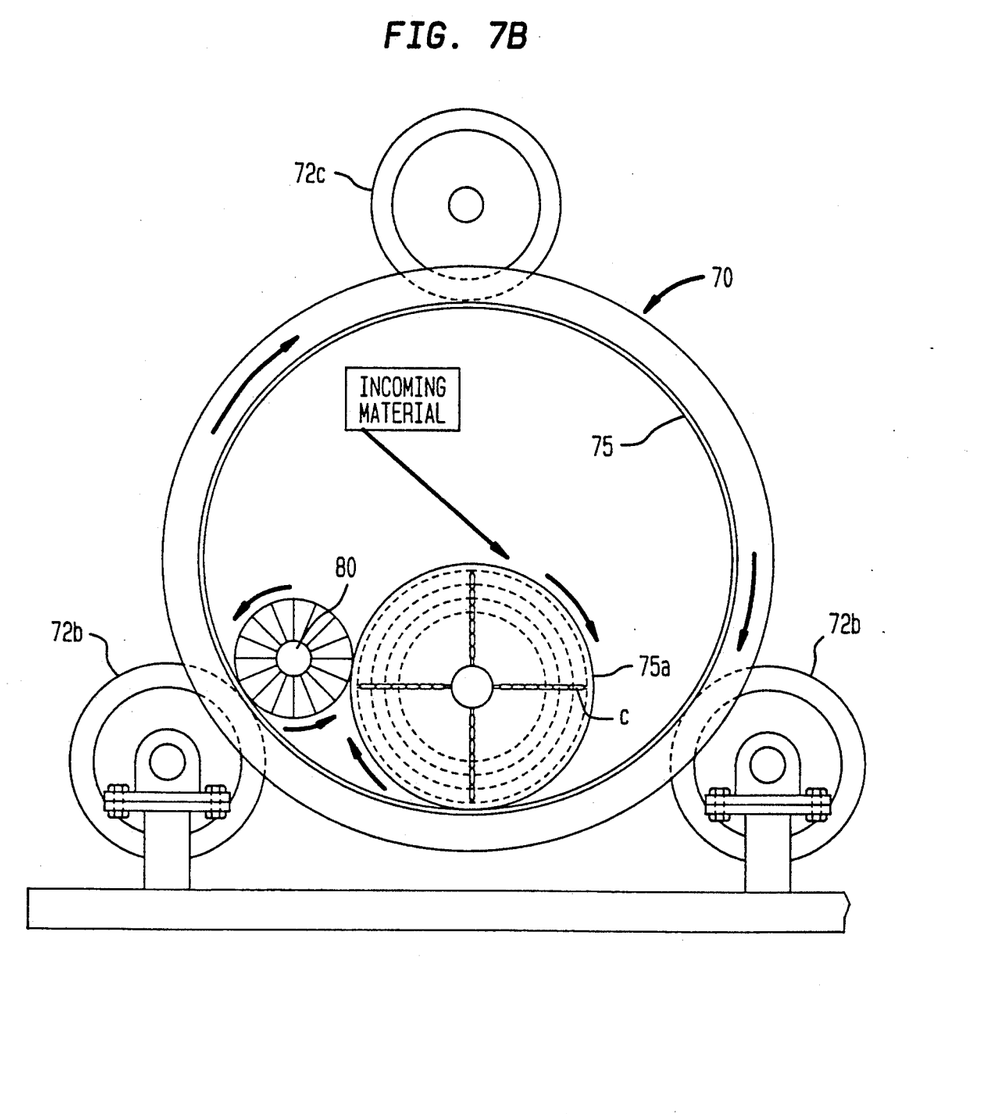
FIG. 7B is a sectional view of the horizontal version of the pulverizer/grinder stage shown in FIG. 7A.

In FIGS. 7A and 7B, another version of the pulverizer/grinder stage 70 is shown having the cylindrical container 75 oriented in the horizontal direction and driven by drive rollers 72b mounted on the drive shaft 72d and driven by the motor 72a. Idler rollers 72c are provided at an upper portion for stabilizing the rotating container. The container includes an attached end wall 74, perforated side walls 75, stationary end wall 76, inlet 77 toward the upper portion of the container, and O-ring seals 71 between the stationary end wall 76 and the rotating side walls 75. The grinder chains C are mounted on a driving arbor 78 which is located off-center from the container axis at a lower portion of the container. The arbor 78 is driven by the motor 78a such that the chain tips pass in close proximity to the container walls. The arbor 78 and chains C are driven in the same direction but at a much higher speed than the cylindrical container 75.

The inlet 77 feeds incoming material which is swept by the motion of the container into the area between the grinder chains and the container walls. A partial casing wall 75a on the interior side of the grinder chains is provided to maintain partially pulverized particles in the area of the chains. A counter-rotating brush 80 is provided for pushing material against the flow created by the rotating cylinder walls 75 and impelling it back toward the chains C. Particles pulverized to a size smaller than the selected size of the perforations 79 pass through the container walls as an output product of non-fermented (mostly plastic) particles P. A screw worm 73 is provided to continually move material in the container toward the chains. The grinder chain assembly and end wall 76 are mounted on rollers 76b for easy replacement of worn parts.

The finely ground material P from the pulverizer/grinder stage 70 can be made into usable construction materials by heating the primarily plastic, granular material in silos to a temperature between about 80° to 120° C., then pouring the melted material into molds and subjecting it to forming pressures of about 100 to 150 kg/cm². When the molded material has cooled, it can be readily removed from the molds. The molded material is of a high strength, has a density of 1.0 to 1.2, and can be used for fence parts, pavement blocks, curbs, underlayments, railroad ties, etc. The plastic material P may also be molded by extrusion, since the result of the processing described above is plastic stock material that is clean enough for extrusion.

Figure 8:
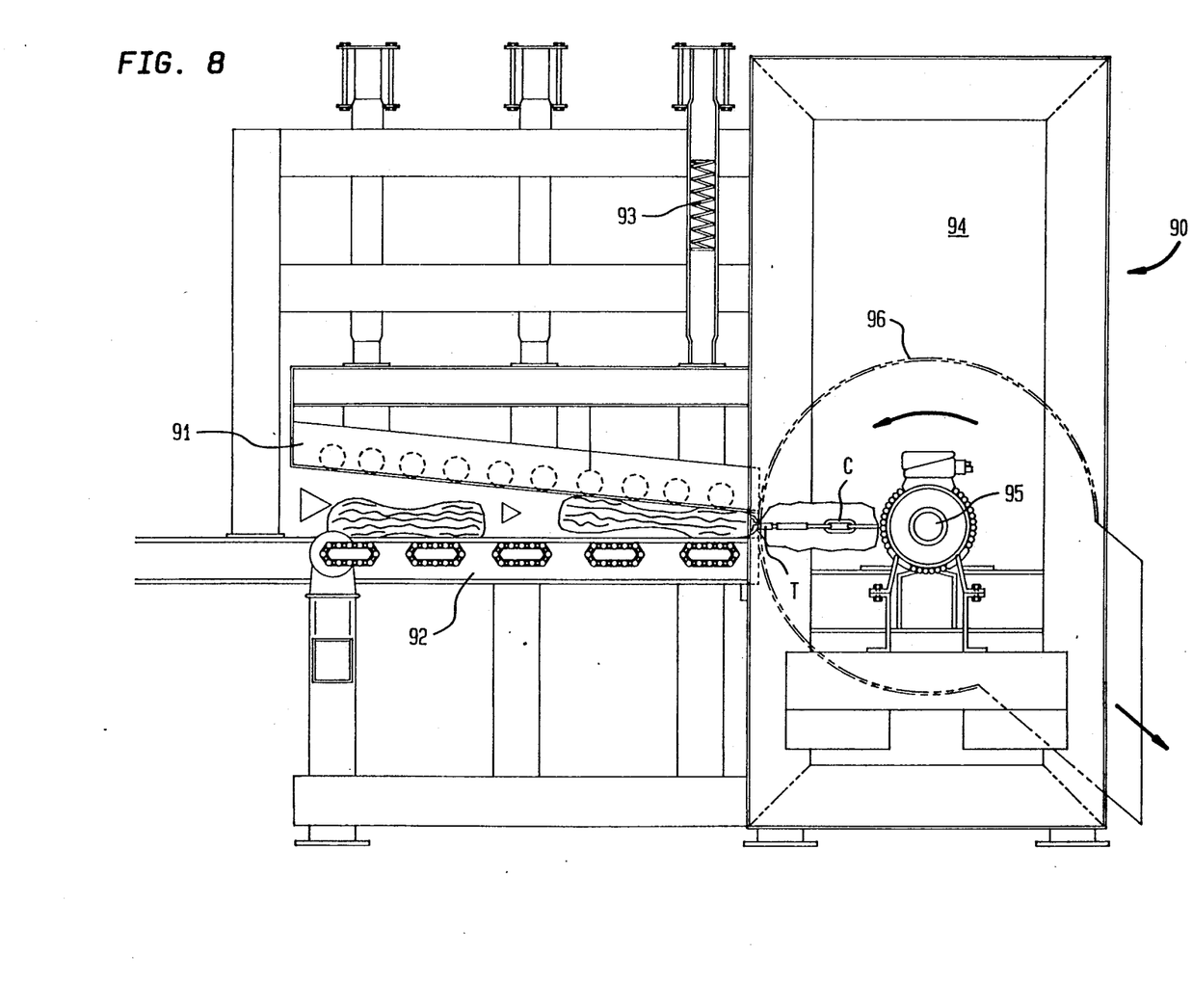
FIG. 8 is a side view of a grinder unit having an axle with grinder chains for shredding old tires into rubber particles.

The above concepts for fragmentation of waste materials using high speed grinder chains may also be applied to other types of solid waste. In FIG. 8, a modified version of a grinder unit 90 is shown adapted for shredding worn tires. The tires are fed between an upper roller way 91 which is inclined at an angle with respect to a lower conveyor drive 92. The inserted tires are progressively compressed as they are advanced under the upper roller way 91 pushed by compression springs 93. A shredder unit 94 has two, three, or four rows of chains C attached at their one end to a drive axle 95 and provided at their other end with sharpened, wear-resistant tips T. The axle is rotated at high speed such that the chains C are stretched out by centrifugal force and their tips T form a cylindrical shredding contour 96. The whirling tips shred the tires fed into the shredder unit 94 into particles about 0.5 mm thick and 5 mm long, including all the rubber treads, nylon cloth, and steel belting. The ferrous particles are removed with an electromagnet drum or hover band. The rubber particles, free of ferrous elements, may be stocked in a silo and heated to between 150° to 200° C. then poured into molds and compression-molded to the desired shape of the output products. The rubber particles may be mixed with the plastic particles obtained from the processing of household waste and heat molded into an aggregate of excellent quality and durability for use, for example, as railroad ties, sidewalk curbing, or pavement blocks.

Although the invention has been described with reference to certain preferred embodiments, it will be appreciated that many variations and modifications may be made consistent with the broad principles of the invention. It is intended that the preferred embodiments and all of such variations and modifications be included within the scope and spirit of the invention, as defined in the following claims.

I claim:

1. An apparatus for transforming an input garbage mixture of fermentable, organic waste materials and non-fermentable and/or non-organic waste materials into separate output products, comprising:

a fermentation stage for depositing an input garbage mixture into non-compacted swathes to allow fermentation of the fermentable, organic waste materials therein;

an input stage for loading the garbage mixture from the fermentation stage to a grinder; and a grinder/separator stage including a grinder for grinding the garbage mixture conveyed from the input stage into smaller particles, and a separator having a screen of a selected mesh size for separating ground waste particles up to the selected mesh size falling therethrough as a fermented output product, and for conveying the remainder of the ground waste particles not falling through the screen to a reject output as a non-fermented output product, wherein the grinder of said grinder/separator stage has walls defining a containment space, at least three rotating axles arranged in parallel in the containment space, each of said axles carrying a plurality of chains mounted by their one ends spaced apart along a horizontal length thereof and provided at their other free ends with a hardened tip, and the axles being spaced apart from each other such that the chains are driven with their tips passing in close proximity to those of the other axles, and further wherein two of the axles are arranged opposite each other at an upstream position of a garbage processing path for receiving the input garbage mixture and are rotated in counter-rotational directions from each other such that their chain tips pass at a point of tangency in close proximity with those of the other axle moving in a same downstream direction, and the third axle is arranged at a downstream position of the garbage processing path in triangular configuration with the two axles at the upstream position and is rotated in the same rotational direction as one of the upstream axles and in a counter-rotational direction to the other of the upstream axles such that its chain tips pass at a point of tangency in close proximity with those of said one upstream axle in counter directions, and pass at a point of tangency in close proximity with those of said other upstream axle moving in a same downstream direction.

2. An apparatus according to claim 1, wherein said input stage is equipped with a hopper for loading the garbage mixture on a conveyor conveying the garbage mixture to the grinder, a dryer for at least partially drying the garbage mixture, and a magnetic picker for picking off ferrous materials from the input garbage mixture.

3. An apparatus according to claim 2, wherein the separator of said grinder/separate stage includes an inclined, rotating trommel formed with the screen in a tunnel shape.

4. An apparatus according to claim 1, wherein the axles are rotated at different rotational speeds.

5. An apparatus according to claim 1, further comprising subsequent grinder/separator stages each having a grinder and a separator similar to those of the first-mentioned grinder/separator stage, except that the separator of each subsequent stage receives the fermented output product from the previous stage, grinds it into finer particles, and separates the ground particles up to the selected finer mesh size.

6. An apparatus according to claim 1, wherein the separator of said grinder/separator stage is equipped with a cleaning device for cleaning the meshes of the screen.

7. An apparatus according to claim 1, wherein the separator of said grinder/separator stage is equipped with an air drying device for drying the garbage mixture conveyed therethrough.

8. An apparatus for transforming an input garbage mixture of fermentable, organic waste materials and non-fermentable and/or non-organic waste materials into separate output products, comprising:

a fermentation stage for depositing an input garbage mixture into non-compacted swathes to allow fermentation of the fermentable, organic waste materials therein;

an input stage for loading the garbage mixture from the fermentation stage to a grinder;

a grinder/separator stage including a grinder for grinding the garbage mixture conveyed from the input stage into smaller particles, and a separator having a screen of a selected mesh size for separating ground waste particles up to the selected mesh size falling therethrough as a fermented output product, and for conveying the remainder of the ground waste particles not falling through the screen to a reject output as a non-fermented output product; and a pulverizer/grinder stage for pulverizing the reject output of said grinder/separator stage into smaller particles, including an enclosed, rotating container having an inlet for the reject material and being defined by cylindrical container walls perforated with holes of a selected size for allowing particles up to the selected size to pass therethrough as a non-fermented output product, and a rotating axle arranged in parallel with a cylinder axis within the cylindrical container and carrying a plurality of chains mounted by their one ends spaced apart along a vertical length thereof and provided at their other free ends with hardened tips, wherein the rotating axle is arranged off-center from a cylinder axis of the cylindrical container, said rotating container and said rotating axle are rotated in the same rotational direction such that the hardened tips on the free ends of the chains of said rotating axle pass at a point of tangency in close proximity to the container walls moving in counter directions for pulverizing the reject material on a garbage processing path therebetween.

9. An apparatus according to claim 8, wherein the cylindrical container has its cylinder axis arranged horizontally, the inlet is arranged at an upper portion of the cylindrical container, the rotating axle is arranged at a lower portion of the cylindrical container, and the cylindrical container is rotated in a direction to bring the input material toward the chains of the rotating axle.

10. An apparatus according to claim 9, wherein the rotating axle is rotated in the same direction as, but at a higher speed than, the cylindrical container, and a counter-rotating brush is arranged at a downstream position of the rotating axle in proximity to the container walls for pushing the material back toward the chains of the rotating axle.

* * * * *